(12) United States Patent
Travers et al.

(10) Patent No.: US 6,583,330 B1
(45) Date of Patent: Jun. 24, 2003

(54) CATALYSTS CONTAINING HETEROPOLYANIONS USABLE IN PROCESSES FOR CONVERSION OF PARAFFINS

(75) Inventors: Christine Travers, Rueil-Malmaison (FR); Maryline Delage, Rueil Malmaison (FR); Eric Benazzi, Chatou (FR); Jean-François Joly, Lyons (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/604,055

(22) Filed: Jun. 26, 2000

(30) Foreign Application Priority Data

Jun. 25, 1999 (FR) .............................. 99/08206

(51) Int. Cl.⁷ .............................. C07C 2/58; C07C 5/13; B01S 27/18
(52) U.S. Cl. .................. 585/721; 502/208; 502/213; 502/214; 502/232; 502/240; 502/254; 502/255; 502/258; 502/261; 502/262; 502/300; 502/325; 502/313; 502/321; 502/322; 502/323; 585/709; 585/713; 585/734
(58) Field of Search ................ 502/208, 213, 502/214, 232, 240, 254, 255, 258, 261, 262, 300, 305, 313, 321, 322, 323; 585/709, 713, 721, 734

(56) References Cited

U.S. PATENT DOCUMENTS

| 3,374,285 A | | 3/1968 | Henke et al. | |
| 5,300,703 A | * | 4/1994 | Knifton | ...................... 568/794 |
| 5,489,733 A | * | 2/1996 | Soled et al. | ................. 585/740 |

FOREIGN PATENT DOCUMENTS

| EP | 0 623 386 A2 | 11/1994 |
| EP | 0 864 354 A1 | 9/1998 |
| WO | WO 95/13869 | 5/1995 |

* cited by examiner

*Primary Examiner*—Elizabeth D. Wood
(74) *Attorney, Agent, or Firm*—Millen, White, Zelano & Branigan, P.C.

(57) ABSTRACT

New catalysts that contain heteropolyanions of the 12-tungstophosphoric acid or the 12-tungstomolybdic acid, and, for some of these, at least one metal of group VIII, and that are deposited on substrates that develop a specific surface area and a high pore volume, such as zirconium oxide ($ZrO_2$), silicas, silica-aluminas or aluminas, are used in particular in isomerization of paraffinic fractions that contain in large part n-paraffins that have, for example, 4 to 8 carbon atoms per molecule and in aliphatic alkylation of isoparaffins (for example isobutane and/or isopentane) by at least one olefin that comprises, for example, 2 to 6 carbon atoms per molecule ($C_2$ to $C_6$).

43 Claims, No Drawings

CATALYSTS CONTAINING HETEROPOLYANIONS USABLE IN PROCESSES FOR CONVERSION OF PARAFFINS

This invention relates to new catalysts that contain heteropolyanions of 12-tungstophosphoric acid or 12-tungstomolybdic acid and, for some of these, at least one metal of group VIII, deposited on substrates that develop a specific surface area and a high pore volume, such as zirconium oxide ($ZrO_2$), silicas, silica-aluminas or aluminas.

These catalysts are used in particular in isomerization of paraffinic fractions that contain in large part n-paraffins that have, for example, 4 to 8 carbon atoms per molecule and in aliphatic alkylation of isoparaffins (for example isobutane and/or isopentane) by at least one olefin that comprises, for example, 2 to 6 carbon atoms per molecule ($C_2$ to $C_6$).

This invention also relates to the preparation of these catalysts.

The elimination of lead and the very short-term reduction of the content of aromatic compounds of the gasolines, combined with the persistent requirement for preserving a high octane number (greater than or equal to 95), led to seeking catalysts and improved processes that make it possible to obtain gasolines with a high octane number, and, among them, the processes for isomerization of paraffinic fractions that contain in large part n-paraffins and aliphatic alkylation of the isoparaffins. These two processes are performed by an acid mechanism that uses carbocations as intermediate reaction products. They require the use of catalysts that develop a high acidity.

For isomerization of paraffinic fractions that contain in large part n-paraffins, these acid solids should result in a good activity at the lowest possible temperature, whereby the thermodynamic equilibrium promotes the low-temperature multibranched isomers.

The catalysts that are commonly used industrially are:
Pt/zeolite catalysts and more particularly Pt/mordenite catalysts,
catalysts with a base of Pt/halogenated alumina, and more particularly strongly chlorinated alumina,
catalysts with a base of sulfated zirconia.

For the aliphatic alkylation, these are the liquid acids HF and $H_2SO_4$ that are used industrially, despite major problems of use and toxicity for the environment.

More recently, catalysts that contain heteropolyanions were studied for these two reactions. These heteropolyanions are generally in the form of salts of the 12-tungstophosphoric acid (U.S. Pat. No. 5,482,733) or of the 12-tungstosilicic acid (EP-A 0 623 386 and U.S. Pat. No. 5,391,532) that are exchanged by aluminum and deposited on various substrates such as $Zr(OH)_4$ or $SiO_2$, or else in the form of 12-tungstophosphoric acid itself, supported on mesoporous solids such as MCM-41 (U.S. Pat. No. 5,366,945).

In the isomerization reaction of the paraffinic fractions that contain in large part n-paraffins, for example with 4 to 8 carbon atoms, the thermodynamic equilibrium between the various isomers varies considerably with the temperature. The branched hydrocarbons, which are those that have a high octane number, are more enhanced, the lower the temperature. The problem of the isomerization of these paraffinic fractions therefore consists in finding active catalysts at the lowest temperature.

As far as the reactions of aliphatic alkylation of isoparaffins by olefins are concerned, it was important to be able to use a solid catalyst that makes it possible to work under the simplest conditions possible and at operating temperatures that are higher than those imposed by the use of standard liquid acids, thus preventing the problems that are associated with cooling.

One of the objects of this invention is therefore to provide new catalysts that are improved in terms of the paraffin conversion reactions as well as in terms of the isomerization reactions of paraffinic fractions that contain in large part n-paraffins in the reactions of aliphatic alkylation of isoparaffins by the olefins.

The catalysts according to this invention are defined in general by the fact that they comprise at least heteropolyanions that are derived from tungstophosphoric acid or 12-tungstomolybdic acid, but preferably 12-tungstophosphoric acid, deposited on substrates that develop a specific surface area and a high pore volume, such as zirconium oxide, silicas, silica-aluminas or aluminas, preferably zirconium oxide.

Some of these catalysts also comprise at least one metal of group VIII. The latter are dedicated in particular to the isomerization of the paraffinic fractions that contain in large part paraffins that have, for example, 4 to 8 carbon atoms. The others, that do not contain a metal of group VIII, are more particularly suited to the aliphatic alkylation of isoparaffins (for example isobutane and/or isopentane) with at least one olefin that comprises, for example, 2 to 6 carbon atoms per molecule ($C_2$ to $C_6$).

The substrate of the catalysts of the invention generally develops a specific surface area of 50 to 500 $m^2/g$, preferably 80 to 500 $m^2/g$, and most often 80 to 450 $m^2/g$, and a pore volume of 0.2 to 0.9 $cm^3/g$, preferably 0.3 to 0.9 $cm^3/g$ and most often 0.3 to 0.8 $cm^3/g$; it is advantageously put in the form of balls or extrudates. The heteropolyanion content is 10 to 55% by weight relative to the entire catalyst, preferably 25 to 50% by weight.

The catalysts according to the invention that are particularly dedicated to the isomerization of paraffinic fractions that contain in large part n-paraffins comprise, in addition to the heteropolyanion and the substrate, at least one metal of group VIII that is selected from among, for example, platinum, palladium, rhodium, nickel and ruthenium in a content of 0.05 to 10% by weight, preferably 0.1 to 5% by weight and more preferably 0.2 to 1% by weight.

For the preparation of the catalysts of the invention, the heteropolyanions that are to be introduced can be obtained from aqueous solutions of corresponding heteropolyacids or salts of these acids. They are deposited on the substrates by any impregnation technique that is known to one skilled in the art and in particular by dry impregnation in the pore volume. Before impregnation, the substrates are advantageously calcined, for example, at a temperature of 200° C. to 800° C., preferably 350° C. to 600° C.

In the case of the catalysts to use in isomerization paraffinic fractions that contain in large part n-paraffins, at least one metal of group VIII is deposited on the substrate by any method that is known to one skilled in the art, for example by impregnation.

The heteropolyanion and the metal of group VIII can be co-impregnated on the substrate from a mixed solution of a precursor of the heteropolyanion (heteropolyacid or one of its salts) and a precursor of the metal of group VIII. At the end of the co-impregnation, the catalyst is dried in a drying oven for 6 to 12 hours at a temperature of 100° C. to 150° C., then calcined under air for a period of 0.5 to 4 hours, preferably 1 to 3 hours, at a temperature of 150° C. to 400° C., preferably 180° C. to 350° C.

The heteropolyanion and the metal of group VIII can also be impregnated consecutively, whereby the heteropolyanion is then preferably impregnated first. In this case, drying and calcination stages that are described above are in general used after the impregnation of the heteropolyanion, then after the impregnation of the metal of group VIII.

Among the above-mentioned metals of group VIII, platinum and palladium are preferred; all of the salts of these metals that are soluble enough in water can be used as precursors.

As a metal of group VIII, platinum can also be introduced into the catalyst by a mechanical mixture with a $Pt/Al_2O_3$ catalyst or $Pt/SiO_2$ catalyst that is reduced in advance.

In the case of catalysts to be used in aliphatic alkylation that do not contain a metal of group VIII, the deposition of heteropolyanions for example by impregnation, as described above, and immediately drying and calcination stages are then carried out.

In all of the cases, at the end of the calcination, in general a treatment under hydrogen is carried out for a period of 0.5 to 4 hours, preferably 1 to 3 hours, at a temperature of 120° C. to 600° C., preferably 150° C. to 500° C.

In the isomerization processes that use catalysts according to the invention, in general feedstocks that contain at least 80% by weight, preferably at least 90% by weight, of paraffins with 4 to 8 carbon atoms are treated. More particularly, C4, C5–C6–, C5–C7 or C8 fractions can be involved.

The feedstock and the hydrogen are brought into contact with a catalyst according to the invention that comprises at least one metal of group VIII, under isomerization conditions. This contact can be carried out by using the catalyst in a fixed bed, a fluidized bed or in batch mode (i.e., intermittently). The isomerization reaction is generally carried out at a temperature of 100° C. to 350° C., preferably 150 to 300° C., at partial $H_2$ pressures that go from atmospheric pressure (0.1 MPa) to 7 MPa, preferably 0.5 MPa to 5 MPa. The volumetric flow rate can be 0.1 to 20, preferably 1 to 10, liters of liquid hydrocarbons per liter of catalyst and per hour. The $H_2$/feedstock molar ratio can vary within broad limits; it is normally 0.8/1 to 20/1, preferably 0.1/1 to 10/1. Whereby the isomerization is a balanced reaction, the isomerate also contains unconverted paraffins (n-paraffins or monobranched paraffins). These paraffins can be separated from isomers, for example by distillation or by fractionation on a molecular sieve and recycled into the isomerization unit.

The performance levels of the catalysts are defined by conversion (C) of n-hexane, selectivity ($S_i$) of isomerization, selectivity of dibranched isomers ($S_d$) and selectivity of cracking ($S_c$).

$$\text{Conversion } (C\ \%) = \frac{(\text{input n-hexane mass} - \text{output n-hexane mass}) \times 100}{\text{input n-hexane mass}}$$

$$\text{Isomerization selectivity } (S_i\ \%) = \frac{\text{sum (masses of } iC6) \times 100}{\text{sum of masses of the reaction products}}$$

$$\text{Dibranched selectivity } (S_d\ \%) = \frac{\text{sum (masses of dibranched isomers)} \times 100}{(\text{sum of masses of reaction products})}$$

$$\text{Cracking selectivity } (S_c\ \%) = \frac{\text{sum (masses of } C_1 \text{ to } C_5) \times 100}{\text{sum of the masses of reaction products}}$$

The catalysts according to this invention that do not contain a metal of group VIII can be used in processes that make it possible to produce under the best conditions the alkylation reaction of an isoparaffin (for example isobutane and/or isopentane) by at least one olefin, for example with 2 to 6 carbon atoms. In particular, said reaction is characterized by a strong exothermicity (about 83.6 kJ/mol) of transformed butene if the olefin is butene and if the isoparaffin is isobutane), the use of the catalysts according to this invention makes it possible to obtain good homogeneity of temperature and concentration of reagents.

In the isoparaffin alkylation process that uses the catalysts of the invention, the operating conditions, and more particularly the temperature and the pressure, are generally selected so that the mixture that consists of the isoparaffin, the olefin(s) and the products of the reaction is liquid. In addition, it is important that the catalyst be immersed in said liquid to ensure a good liquid-solid contact.

The catalyst of the invention is advantageously used in the reaction zone for alkylation of the isoparaffin (isobutane and/or isopentane) with at least one olefin that comprises 2 to 6 carbon atoms per molecule, in liquid phase and mixed with the isoparaffin and/or a mixture of isoparaffins. The catalyst according to the invention can be used in an expanded bed, in a reaction zone that is almost perfectly stirred or in a circulating bed; preferably it is used in a process that uses a continuous liquid phase, whereby the catalyst can be used in suspension form according to the two preferred implementations described below.

A first preferred implementation of the catalyst of the invention is the reaction zone with an almost perfect mixture, i.e., with a perfect or near-perfect mixture (stirred tank or Grignard tank) that uses at least one stirring means, for example at least one propeller to obtain an adequate stirring of the catalyst in suspension in the hydrocarbon liquid phase, which generally comprises isoparaffin (isobutane and/or isopentane), at least one olefin, optionally at least one inert diluent (for example propane and n-butane) and the alkylation reaction products. The feedstock that is to be converted and that consists of isobutane and/or isopentane and at least one olefin can be, for example, introduced in liquid form at at least one point within the hydrocarbon liquid phase that is present in the reaction zone.

A second preferred implementation of the catalyst according to this invention in suspension in a hydrocarbon phase is the co-current moving bed, i.e., the circulating bed. In this implementation, the catalyst that is in suspension in the hydrocarbon liquid phase and that generally comprises isoparaffin (isobutane and/or isopentane), at least one olefin, optionally at least one inert diluent (for example propane or n-butane) and products of the alkylation reaction, circulates from bottom to top in the reaction zone. The unit that consists of the catalyst suspension in the hydrocarbon phase then circulates through at least one heat exchanger and at least one pump before again being introduced into the inlet of the reaction zone. The feedstock that is to be converted and that consists of isobutane and/or isopentane and at least one olefin is introduced either in liquid form or in gaseous form at at least one point of the reaction zone.

In the two types of implementations that are described above, the isoparaffin (isobutane and/or isopentane) that has not been converted or has been introduced in excess relative to the stoichiometry of the reaction is generally recycled after separation of the alkylate, either by direct introduction into the reaction zone or by mixing with the feedstock that is to be converted.

The isoparaffin(s)-olefin(s) mixture is generally introduced into the reaction zone at an hourly volumetric flow rate that is expressed by weight of olefin introduced per unit of weight of the catalyst and per hour (pph), 0.001 to 10 h$^{-1}$, preferably 0.002 to 2 h$^{-1}$. Said mixture can also be produced inside the reaction zone. In all of the cases, the mixture that is thus constituted is, in the reaction zone, under pressure and temperature conditions such that it remains liquid in the catalyst.

The reaction temperature is generally 0° C. to 300° C., preferably 20° C. to 200° C. The pressure of the reaction zone is generally enough to maintain the hydrocarbons in liquid state in said zone.

To limit the secondary reactions, excess isoparaffin is generally used relative to the olefin. As an example, in the case of the alkylation of isobutane by a butene, isobutane can be introduced in a pure state in the feedstock or in the form of a mixture of butanes containing, for example, at least 40% of isobutane. In addition, it is possible to introduce a pure butene or else a mixture of isomer butenes. In all of the cases, the isobutane/butene(s) molar ratio in the feedstock is generally 1/1 to 100/1, preferably 3/1 to 50/1 and often preferably 5/1 to 15/1.

When the nature of the catalyst and the reaction conditions are selected judiciously (in particular the temperature), the catalyst according to the invention makes possible the production of alkylation products of at least one isoparaffin by at least one olefin that are advantageous as fuels and gasoline components for engines and that comprise, for example, at least 60% mol of paraffins that have 8 carbon atoms per molecule and less than 1% mol of unsaturated compounds, whereby the paraffins comprise 8 carbon atoms per molecule comprising 70 to 98% mol of trimethylpentanes.

Another advantage of the catalyst according to this invention is the possibility of alkylating, at a low temperature, the isobutane with mixtures of olefins comprising 2 to 6 carbon atoms per molecule, where the ratio of olefins that comprise more than 4 carbon atoms per molecule is very large.

The following examples explain the invention without limiting its scope.

EXAMPLE 1

Catalyst A (In Accordance with the Invention)

49.85 g of 12-tungstophosphoric acid (H$_3$PW$_{12}$O$_{40}$) is dissolved in 30 cm$^3$ of water. This solution is impregnated in the pore volume of 49.85 g of a zirconium oxide substrate. The solid that is thus obtained is then dried for 12 hours in a drying oven at 120° C. and then calcined for 2 hours at 200° C. under air. 0.3% by weight of platinum is then added by mechanical mixing under inert atmosphere of the solid prepared above, with a catalyst Pt/Al$_2$O$_3$ that is reduced in advance.

EXAMPLE 2

Catalyst B (In Accordance with the Invention)

49.85 g of 12-tungstophosphoric acid (H$_3$PW$_{12}$O$_{40}$) is added to 9.5 g of an H$_2$PtCl$_6$ solution that contains 3.15% by weight of platinum. The volume of the solution is then adjusted to 30 cm$^3$. This solution is then impregnated in the pore volume of 49.85 g of a zirconium oxide substrate.

The catalyst that is thus obtained is dried for 12 hours in the drying oven at 120° C., then calcined for 2 hours at 200° C. under air before being treated under H$_2$ at 220° C. for 4 hours.

EXAMPLE 3

Isomerization Test of the n-Hexane

Catalysts A and B that are prepared in Examples 1 and 2 are tested in isomerization of n-hexane at 200° C.; H2/HC (mol)=10; VVH=2 h$^{-1}$; and under a pressure of 0.4 MPa. The respective performance levels of these catalysts are provided in Table 1 below.

TABLE 1

|  | Catalyst A | Catalyst B |
| --- | --- | --- |
| nC$_6$ conversion (%) | 71.1 | 68.3 |
| Total isomerization selectivity (%) | 94.7 | 98.85 |
| Dibranched isomer selectivity (%) | 21.9 | 28.3 |
| Cracking selectivity (%) | 5.3 | 1.15 |

Upon iso-conversion, catalyst B that is prepared by co-impregnation of heteropolyacid and platinum has a considerably improved isomerization selectivity, which is accompanied by a greatly reduced cracking.

EXAMPLE 4

Continuous Aliphatic Alkylation Test

The catalyst that is used in aliphatic alkylation differs from the catalyst that is described in Example 1 in that it does not contain platinum; the preparation is ended after the calcination stage under air.

36 g of this catalyst is introduced into a perfectly stirred Grignard-type 500 ml reactor that is equipped with mechanical stirring, an inlet that makes it possible to inject feedstock and an outlet for recovering the formed products.

The reactor is then filled with liquid isobutane.

The reactor is then heated to a temperature of 90° C., and the mechanical stirring is operated at a speed of 600 rpm. Then, a feedstock that contains 10% of butene-2 and 90% of isobutene (iC$_4$/butene-2 molar ratio=8.7 mol/mol) is injected continuously into the reactor at a flow rate of 30 g of feedstock per hour, or a pph of 0.083 g of butene-2 per gram of catalyst and per hour.

The pressure in the reactor is such that the reaction medium is liquid at the temperature of the reaction.

After 95 hours of injection of the feedstock, the alkylate (C$_{5+}$) that is obtained has the composition that is posted in Table 2 presented below.

The conversion of the olefin is greater than 99.8%, and the age of the catalyst is then about 15.7 grams of C$_{5+}$ alkylate that is formed per gram of catalyst. It is determined by taking into account the fact that the alkylation yield is close to 200% by weight relative to the olefin. Actually, the products that constitute the C$_{5+}$ alkylate are for the most part compounds that have a number of carbon atoms that is double that of the starting olefin.

EXAMPLE 5

This example differs from Example 4 basically by the reaction temperature and the pph. Actually, the reactor temperature is 105° C., and the pph is 1.2 g of butene-1 per gram of catalyst and per hour. In this case, the olefin that is used is butene-1 plus butene-2.

The composition of the alkylate that is obtained after 72 hours of injection of the feedstock is posted in Table 2 below.

TABLE 2

|  | Example 4 | Example 5 |
|---|---|---|
| $(C_5-C_7)/C_{5+}$ | 6.8 | 8.3 |
| $C_8$ (%) | 88.9 | 80.4 |
| $C_{9+}$ (%) | 4.3 | 11.3 |
| TMP*/$C_8$ | 89.1 | 83.8 |

*TMP = trimethylpentanes

What is claimed is:

1. A catalyst that comprises at least one group VIII metal in a content of 0.05 to 10% by weight relative to the entire catalyst and heteropolyanions of 12-tungstophosphoric acid deposited on a zirconium oxide substrate having a specific surface area of 50 to 500 m²/g and a pore volume of 0.3 to 0.9 cm³/g, wherein the heteropolyanion content is 10 to 55% by weight relative to the entire catalyst.

2. A catalyst according to claim 1, wherein the substrate has a specific surface area of 80 to 500 m²/g.

3. A catalyst according to claim 1, wherein the metal of group VIII is selected from the group consisting of platinum, palladium, rhodium, nickel and ruthenium and is present in the catalyst in a content of 0.1 to 5% by weight relative to the entire catalyst.

4. A process for preparation of a catalyst according to claim 1, comprising depositing heteropolyanions of 12-tungstophosphoric acid on the substrate.

5. A process for preparation of a catalyst according to claim 1, wherein heteropolyanions of 12-tungstophosphoric acid as well as a precursor of the metal of group VIII are deposited on the substrate.

6. A process comprising conducting isomerization of paraffinic fractions that contain in large part paraffins that have 4 to 8 carbon atoms per molecule, under isomerizing conditions in contact with a catalyst according to claim 1.

7. A process according to claim 6, wherein the paraffinic fraction is a C4, C5–C6, C5–C7 or C8 fraction.

8. A process comprising conducting aliphatic alkylation of at least one isoparaffin by at least one olefin that comprises 2 to 6 carbon atoms per molecule, under alkylating conditions in contact with a catalyst according to claim 1.

9. A process according to claim 8 wherein the isoparaffin is isobutane or isopentane.

10. A process comprising conducting isomerization of paraffinic fractions containing paraffins having 4 to 8 carbon atoms per molecule, under isomerizing conditions in contact with a catalyst according to claim 3.

11. A catalyst according to claim 1, wherein the heteropolyanion content is 25 to 50% by weight relative to the entire catalyst.

12. A catalyst according to claim 1, wherein the substrate has a specific surface area of 80 to 450 m²/g and a pore volume of 0.3 to 0.8 cm³/g.

13. A catalyst according to claim 11, wherein the substrate has a specific surface area of 80 to 450 m²/g and a pore volume of 0.3 to 0.8 cm³/g.

14. A process comprising conducting isomerization of paraffinic fractions that contain in large part paraffins that have 4 to 8 carbon atoms per molecule, under isomerizing conditions in contact with a catalyst according to claim 12.

15. A process comprising conducting isomerization of paraffinic fractions that contain in large part paraffins that have 4 to 8 carbon atoms per molecule, under isomerizing conditions in contact with a catalyst according to claim 13.

16. A process comprising conducting isomerization of paraffinic fractions that contain in large part paraffins that have 4 to 8 carbon atoms per molecule, under isomerizing conditions in contact with a catalyst according to claim 11.

17. A process comprising conducting aliphatic alkylation of at least one isoparaffin by at least one olefin that comprises 2 to 6 carbon atoms per molecule, under alkylating conditions in contact with a catalyst according to claim 12.

18. A process comprising conducting aliphatic alkylation of at least one isoparaffin by at least one olefin that comprises 2 to 6 carbon atoms per molecule, under alkylating conditions in contact with a catalyst according to claim 13.

19. A process comprising conducting aliphatic alkylation of at least one isoparaffin by at least one olefin that comprises 2 to 6 carbon atoms per molecule, under alkylating conditions in contact with a catalyst according to claim 11.

20. A catalyst that comprises at least one group VIII metal in a content of 0.05 to 10% by weight relative to the entire catalyst and heteropolyanions of 12-tungstomolybdic acid deposited on a zirconium oxide substrate having a specific surface area of 50 to 500 m²/g and a pore volume of 0.3 to 0.9 cm³/g, wherein the heteropolyanion content is 10 to 55% by weight relative to the entire catalyst.

21. A catalyst according to claim 20, wherein the substrate has a specific surface area of 80 to 500 m²/g.

22. A process for preparation of a catalyst according to claim 20, wherein heteropolyanions of 12-tungstomolybdic acid as well as a precursor of the metal of group VIII are coimpregnated on the substrate.

23. A process comprising conducting isomerization of paraffinic fractions that contain in large part paraffins that have 4 to 8 carbon molecule, under isomerizing conditions in contact with a catalyst according to claim 20.

24. A process according to claim 23, wherein the paraffinic fraction is a C4, C5–C6, C5–C7 or C8 fraction.

25. A process comprising conducting aliphatic alkylation of at least one isoparaffin by at least one olefin that comprises 2 to 6 carbon atoms per molecule, under alkylating conditions in contact with a catalyst according to claim 20.

26. A process according to claim 25, wherein the isoparaffin is isobutane or isopentane.

27. A catalyst according to claim 20, wherein the metal of group VIII is selected from the group consisting of platinum, palladium, rhodium, nickel and ruthenium and being present in the catalyst in a content of 0.05 to 10% by weight relative to the entire catalyst.

28. A catalyst according to claim 1, wherein the group VIII metal is platinum.

29. A catalyst according to claim 1, wherein the group VIII metal is palladium.

30. A catalyst according to claim 1, produced by a process comprising coimpregnating a precursor of the group VIII metal and the heteropolyanions of 12-tungstophosphonic acid onto the zirconium oxide substrate.

31. A catalyst according to claim 2, produced by a process comprising coimpregnating a precursor of the group VIII metal and the heteropolyanions of 12-tungstophosphonic acid onto the zirconium oxide substrate.

32. A catalyst according to claim 3, produced by a process comprising coimpregnating a precursor of the group VIII metal and the heteropolyanions of 12-tungstophosphonic acid onto the zirconium oxide substrate.

33. A catalyst according to claim 11, produced by a process comprising coimpregnating a precursor of the group VIII metal and the heteropolyanions of 12-tungstophosphonic acid onto the zirconium oxide substrate.

34. A catalyst according to claim 12, produced by a process comprising coimpregnating a precursor of the group VIII metal and the heteropolyanions of 12-tungstophosphonic acid onto the zirconium oxide substrate.

35. A catalyst according to claim 13, produced by a process comprising coimpregnating a precursor of the group VIII metal and the heteropolyanions of 12-tungstophosphonic acid onto the zirconium oxide substrate.

36. A catalyst according to claim 28, produce by a process comprising coimpregnating a precursor of the group VIII metal and the heteropolyanions of 12-tungstophosphonic acid onto the zirconium oxide substrate.

37. A catalyst according to claim 29, produced by a process comprising coimpregnating a precursor of the group VIII metal and the heteropolyanions of 12-tungstophosphonic acid onto the zirconium oxide substrate.

38. A catalyst according to claim 20, wherein the group VIII metal is platinum.

39. A catalyst according to claim 20, wherein the group VIII metal is palladium.

40. A catalyst according to claim 38, produced by a process comprising coimpregnating a precursor of the group VIII metal and the heteropolyanions of 12-tungstomolybdic acid onto the zirconium oxide substrate.

41. A catalyst according to claim 39, produced by a process comprising coimpregnating a precursor of the group VIII metal and the heteropolyanions of 12-tungstomolybdic acid onto the zirconium oxide substrate.

42. A process comprising conducting isomerization of paraffinic fractions that contain in large part paraffins that have 4 to 8 carbon atoms per molecule, under isomerizing conditions in contact with a catalyst according to claim 38.

43. A process comprising conducting aliphatic alkylation of at least one isoparaffin by at least one olefin that comprises 2 to 6 carbon atoms per molecule, under alkylating conditions in contact with a catalyst according to claim 38.

* * * * *

UNITED STATES PATENT AND TRADEMARK OFFICE
CERTIFICATE OF CORRECTION

PATENT NO. : 6,583,330 B1
DATED : June 24, 2003
INVENTOR(S) : Christine Travers et al.

It is certified that error appears in the above-identified patent and that said Letters Patent is hereby corrected as shown below:

Column 8,
Line 27, reads "carbon molecule" should read -- carbon atoms per molecule --

Signed and Sealed this

Seventeenth Day of August, 2004

JON W. DUDAS
*Acting Director of the United States Patent and Trademark Office*